United States Patent [19]

Perry

[11] 4,384,477
[45] May 24, 1983

[54] SENSING DEVICE

[75] Inventor: Ralph A. Perry, Indianapolis, Ind.

[73] Assignee: Emhart Industries, Inc., Indianapolis, Ind.

[21] Appl. No.: 197,953

[22] Filed: Oct. 17, 1980

[51] Int. Cl.³ ............................................. G01N 25/18
[52] U.S. Cl. .................................................. 73/61.1 R
[58] Field of Search ............... 73/61.1 R, 53, 322.5; 340/603, 618; 114/267; 156/659.1; 427/304

[56] References Cited

U.S. PATENT DOCUMENTS

| 2,660,194 | 11/1953 | Hoffman | 114/267 X |
| 3,720,797 | 3/1973 | Gunn et al. | 73/61.1 R X |
| 3,918,034 | 11/1975 | Orth, Jr. | 73/448 X |
| 3,946,625 | 3/1976 | Miyazaki et al. | 73/61.1 R |
| 4,116,045 | 9/1978 | Potter | 73/61.1 R |
| 4,131,773 | 12/1978 | Maham et al. | 73/61.1 R X |
| 4,221,125 | 9/1980 | Oliver et al. | 73/61.1 R |
| 4,223,552 | 9/1980 | Goldstein | 73/61.1 R |

FOREIGN PATENT DOCUMENTS

| 2601410 | 7/1977 | Fed. Rep. of Germany | 73/61.1 R |
| 2837920 | 3/1980 | Fed. Rep. of Germany | 73/61.1 R |
| 52-17891 | 2/1977 | Japan | 73/61.1 R |

Primary Examiner—E. R. Kazenske
Assistant Examiner—Joseph W. Roskos
Attorney, Agent, or Firm—Robert F. Meyer; David W. Gomes

[57] ABSTRACT

A sensing device for detecting a substance including hydrocarbons on the surface of water provides a floatation device for floating on the water surface and for supporting at least one sensing element for detecting said substance, the floatation device being composed substantially of nitrile. A sensing device for use in an apparatus for detecting a substance on the surface of a liquid, the sensing device providing a mounting surface adapted for facing downwardly toward the liquid surface, a plurality of sensing elements each of which is mounted at a different predetermined distance below the mounting surface, and a flotation portion affixed to the mounting surface for supporting the mounting surface at the liquid surface whereby the sensing elements may be maintained at different known depths below the liquid surface.

8 Claims, 7 Drawing Figures

SENSING DEVICE

BACKGROUND OF THE INVENTION

1. Field of the Invention

The present invention generally relates to sensing devices employing floatation means for supporting a sensing element near the surface of a liquid and, in particular, to such devices as used for detecting hydrocarbon substances on the surface of ground water.

2. Statement of the Prior Art

Wide spread use of fossil fuels in today's world has caused many problems with the pollution of ground water and drinking water supplies by leakage of such fuels and various hydrocarbon containing substances into the ground water. To help detect this problem, sensors have been developed for detecting the presence of such substances on the surface of ground water. One such sensing device is described in U.S. Pat. No. 4,221,125 which employs a semiconductor diode positioned in proximity to the surface of a body of water by a float means for detecting the presence of hydrocarbon substances. A related device is described in U.S. Pat. No. 4,223,552. It has been found, however, that additional information is also desirable such as knowing the amount of hydrocarbons present on the surface of ground water and either the rate of increase or decrease of the hydrocarbon substances present. Problems, however, have been encountered in the reliability of long term sensing devices due to the corrosion of the floatation means caused by various chemical substances present in the ground water and the subsequent dislocation of the sensing element supported thereby in respect to the water's surface.

SUMMARY OF THE INVENTION

Accordingly, an improved sensing device has been developed which insures the reliability of the floatation means in the presence of various corrosive substances and further allows information to be generated with respect to the amount of hydrocarbon substances present on the surface of a liquid. The present invention generally includes a sensing device for detecting a substance including hydrocarbons on the surface of water, comprising a floatation means for floating on the water and for supporting at least one sensing element for detecting the substance, the floatation means being composed substantially of nitrile. The present invention further includes a sensing device for detecting a substance on the surface of a liquid comprising, a mounting surface adapted for facing downwardly toward the liquid surface, a plurality of sensing elements each of which is mounted at a different predetermined distance below the mounting surface, and floatation means affixed to the mounting surface for supporting the mounting surface at the liquid surface whereby the sensing elements may be maintained at different known depths below the liquid surface.

BRIEF DESCRIPTION OF THE DRAWINGS

The present invention is illustratively described with respect to the appended drawings in which.

DETAILED DESCRIPTION OF THE DRAWINGS

Figure 1:
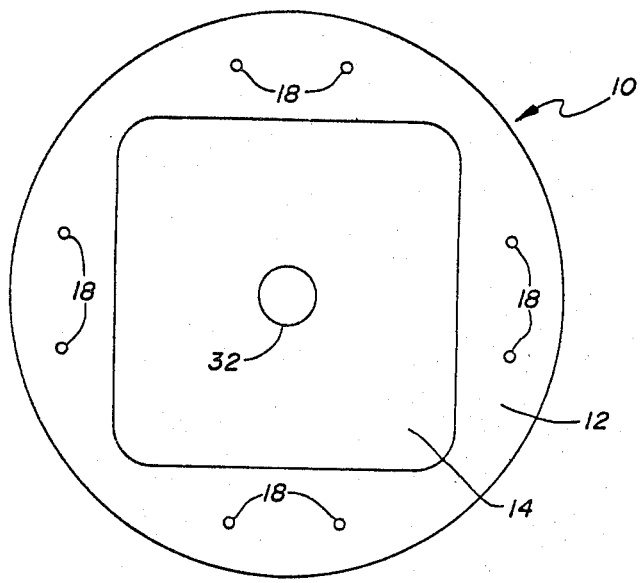
FIG. 1 is a bottom view of a sensing device member constructed according to one embodiment of the present invention.
Figure 2:
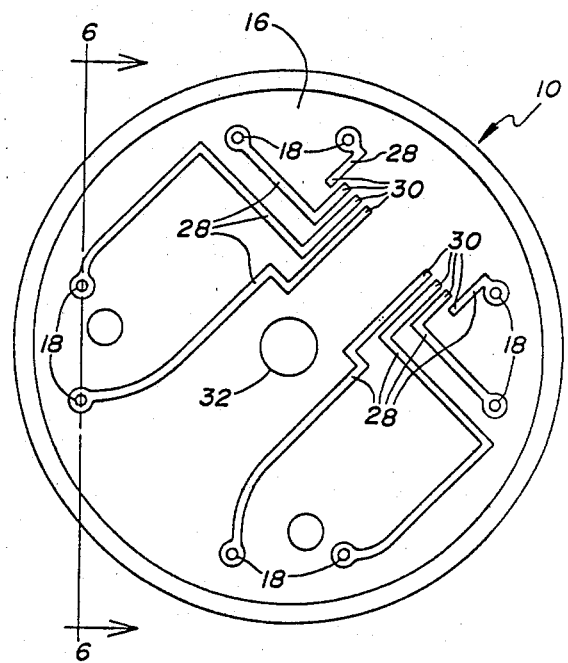
FIG. 2 is a top view of the member of FIG. 1.
Figure 3:
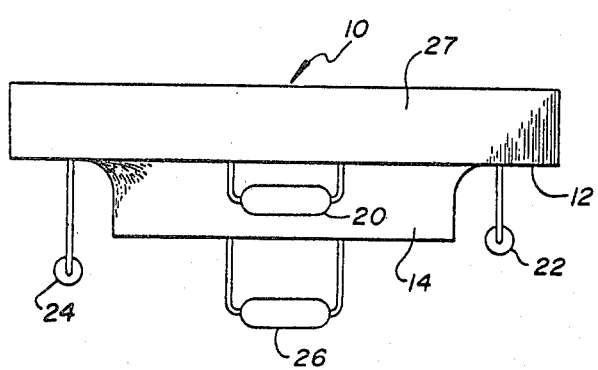
FIG. 3 is a side view of the member of FIGS. 1 and 2 further including a plurality of sensing elements.

In respect to FIGS. 1, 2 and 3, member 10 of a sensing device is shown with bottom, top and side views, respectively. The member 10 generally includes a mounting surface 12, a floatation means 14, and a top surface 16. The downwardly facing mounting surface 12 includes a plurality of apertures 18 in which sensing elements may be mounted. The apertures 18 are arranged in pairs to allow use of dual leaded sensing elements. The sensing elements 20, 22, 24 and 26 are shown in FIG. 3 extending from the apertures 18 to various distances from the downwardly facing surface 12. The sensing elements 20, 22, 24 and 26 are dual leaded semiconductor junction devices or diodes. The upper ends of the apertures 18 are shown extending to the upper surface 16 in FIG. 2.

The floatation means 14 extends downwardly from the mounting surface 12 and is intended to exhibit a positive bouyancy in whatever medium is chosen for the sensor to operate. The size of the floatation means 14 is designed to cause the mounting surface 12 to be located at the surface of the liquid in which the device is operating. By these means, the sensing elements, which are located at predetermined distances from mounting surface 12, are held at known distances below the liquid surface. This allows accurate measurements to be taken of the depth of the substances located on top of the liquid medium.

The entire sensing device member 10 including the floatation means 14 and an upper section 26 forming the mounting surface 12 and the upper surface 16 is made from a closed cell foamed neoprene rubber generically known as nitrile and available under the tradename NITROPHYL from Rogers Corporation of Willimantic, Conn. The material nitrile is useful in the applications of the present invention because it exhibits resistance to chemical decomposition when exposed to a variety of substances including hydrocarbons. Thus, when used to detect the presence of hydrocarbons on the surface of ground water, the nitrile does not decompose when exposed to either ground minerals or the hydrocarbon substances.

The top surface 16 is used for connecting the sensing elements 20, 22, 24 and 26 to an electrical cable for eventual connection to a sensing or measurement instrument (not shown). The top view of the sensing device member 10 shows a plurality of printed circuit lands deposited on the top surface 16, which lands 28 each has one end thereof located in proximity to each of the apertures 18. These ends are so located to allow connection of the sensing elements thereto by such means as soldering. The lands 28 each have another end 30, all of which are proximally located to allow connection thereof to a multiconductor cable. The lands 29 are directly deposited on the surface of the nitrile to avoid the use of a separate printed circuit board in addition to the construction of the member 10. The process by which the printed circuit lands are so formed on the surface of nitrile is covered by one or more of U.S. Pat. Nos. 3,956,041; 4,160,050; 4,144,118, which patents are assigned to the Kollmorgen Corporation. The application of the printed circuit lands 28 to the nitrile was performed for the present embodiment by PCK Technology of Glen Cove, N.Y.

As shown in FIGS. 1 and 2, a central aperture 32 is located through the middle of the member 10 for allowing slidable mounting of the member 10 on a vertical member facilitating the ability of the member 10 to follow the level of the liquid or water being monitored.

Figure 4:
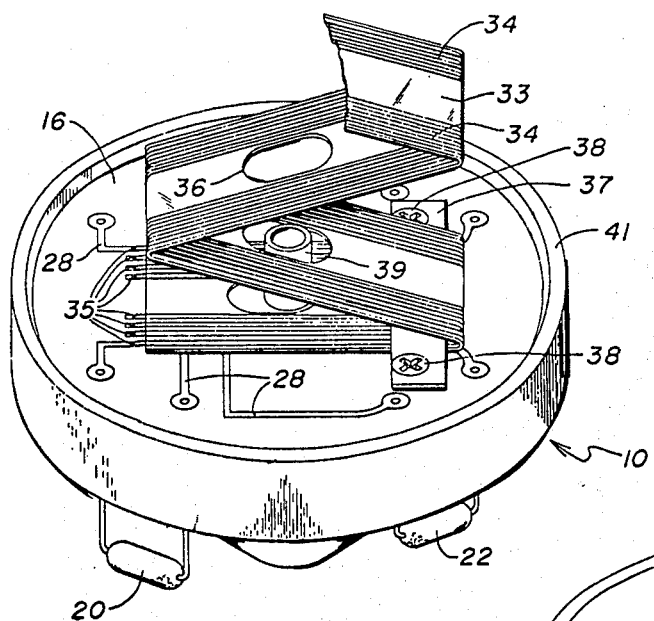
FIG. 4 is a perspective view of the member as shown in FIG. 2 including electrical conductors connected thereto.

FIG. 4 shows the sensing device 10 having an electrical conductor in the form of a ribbon cable 33 connected to the lands 28. The cable 33 used for the present embodiment is available from Amp Incorporated under part No. 5107-1202-2. The cable includes eight separate conductors 34 located along the edges of the cable 33 in pairs of four. Each of the conductors 34 has a terminal 35 connected to the end thereof which terminals 35 are soldered to the separate lands 28 at their ends 30. The cable 33 is modified by the inclusion of a series of holes 36 located approximately midway between the folds of the cable. In the present embodiment, a guide cable (not shown) passes through the holes 36. During construction, the cable is initially held to the top surface of the device 10 by means of a strain relief bar 37 which is secured by a pair of screws 38 to the top surface 16 of the device 10. FIG. 4 further shows a guide pipe means 39 which is secured within the aperture 32 of FIG. 2. In operation, a guide cable is located through the holes 36 and the guide pipe 39 to stabilize the sensing device from lateral movement but to allow vertical movement in accordance with changes in water level.

Figure 5:
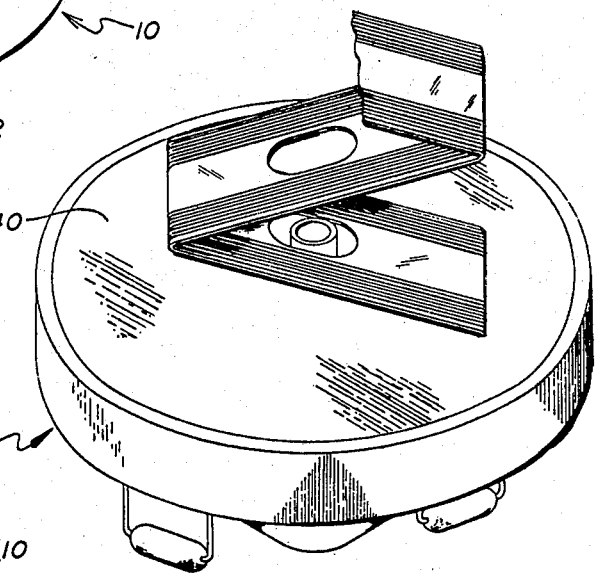
FIG. 5 is a perspective view of the member of FIG. 4 shown in final form for use as a sensing element.

FIG. 5 shows the sensing device 10 as assembled in FIG. 4 and further including an expoxy resin sealant 40 located over the top of surface 16. During construction of the device 10, a peripheral ridge 41 located around the surface 16 helps to confine the liquid epoxy mixture prior to its setting. Any suitable epoxy mixture may be used for the sealant covering 40. One such mixture is described below in reference to FIG. 7.

Figure 6:
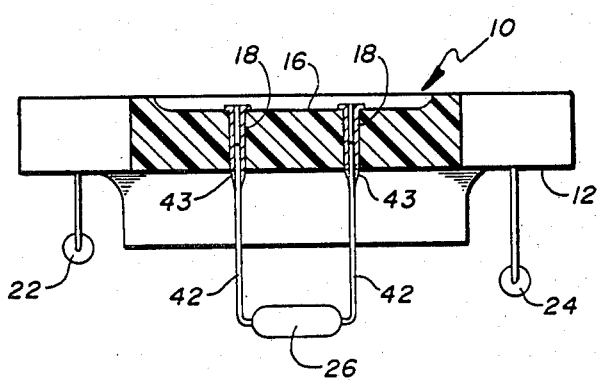
FIG. 6 is a partially sectioned view taken along view line 6—6 of FIG. 2 of the sensing device member as shown in FIG. 3.
Figure 7:
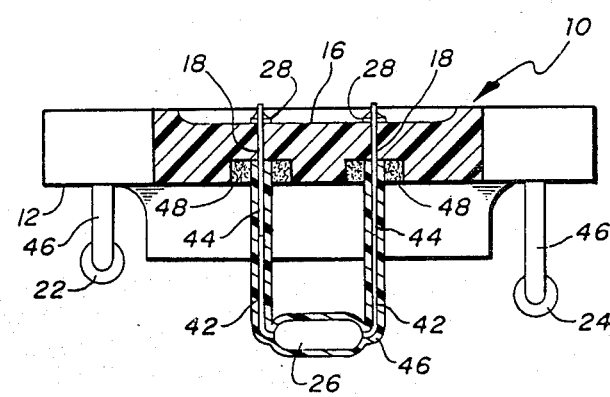
FIG. 7 is a partially sectioned view similar to FIG. 6 but showing a different version for the mounting of the sensing elements.

FIGS. 6 and 7 show partially sectional views of the sensing device member 10 having a plurality of sensing elements 22, 24 and 26 mounted thereon. The sections are taken along view lines 6—6 of FIG. 2 and show two different means for mounting the sensing element 26, either of which means may be used for the other elements 20, 22 and 24. In FIG. 6, the apertures 18 are shown as being plated through from the upper surface 16 to the lower mounting surface 12. By this means, the sensing element 26 is mounted to the member 10 and electrically connected by the soldering of its leads 42 at the points 43 which points are the lower extremities of the plated through apertures 18. The plating on the inside of apertures 18 is made as a part of the lands 28 located on the upper surface 16 and thus no further coupling is needed thereto. In FIG. 7, the apertures 18 are not plated through and thus the leads 42 must extend all the way therethrough in order to be connected to the lands 28. This connection may be made by any means such as soldering. In the case of sensing elements such as 26 which extend to some distance below the mounting surface 12, the leads 42 thereof must be extended. In this case, the extension is formed by a pair of electrical leads 44 which are butt-welded at their ends to the ends of leads 42. The leads 44 are made of nickel for their low thermal conductivity characteristics.

The sensing elements 22, 24 and 26 are shown encased in electrical insulation 46. The insulation shown is commonly known as shrink tubing and is available from Amp Incorporated under part No. 603342-1. The tubing used is clear in color and has a minimized thickness to reduce desensitizing effects on the sensing elements. In the present embodiment, tubing having a thickness of 0.015 inches (0.38 millimeters) or less is used. the ends of the tubing extend into a pair of recesses 48 located in the bottom mounting surface 12 and are sealed thereto by an epoxy sealant contained within said recesses 48. Any suitable epoxy resin will suffice and the material used for the present embodiment is Isochem 401 NV clear with an aliphatic amine curing agent, Isochem 9/22 hardner, with a Thermoset 50Z black coloring in the ratio of 75%-22%-3%, respectively. These are available from Isochem Resins, Inc., of Lincoln, R.I. Thus mounted, the sensing element or diode is very well insulated from the environment in which it is located. Because the sensing device depends upon measurement of the current flowing through the various elements or diodes, it is important that leakage current between the leads 42 and 44 not be allowed to flow. Such leakage current would usually be caused by substances located in the liquid being monitored such as ground water minerals and the like. The combination of the shrink tubing surrounding the diode and the sealing of the ends thereof to the float or member 10 electrically isolate the diode from the liquid being monitored and thus block any such leakage current.

Thus, the present invention provides a means for increasing the amount and reliability of information derived from the sensing device. The mounting surface located at the liquid or water surface allows for easy construction of a sensing device having sensing elements which will be located at various depths below the liquid surface and thus be capable of measuring both the thickness of the hydrocarbons substances present and their rate of increase or decrease. The use of nitrile for the floatation means of the sensing device provides a stable substance which will not be corroded by various substances present in ground water supplies including hydrocarbon containing substances. This enables the sensing device to operate over extended periods of time which may include a constant monitoring of hydrocarbon substances present for that entire period. The resistivity of the nitrile material to various corrosive substances insures the location of the sensing elements at the proper liquid depth over the extended periods of time.

The present invention relates in subject matter to two copending patent applications for "SENSING DEVICE" by Ralph A. Perry and Raymond J. Andrejasich Ser. No. 197,555, and "SENSING DEVICE" By Ralph A. Perry and James M. Booe, Ser. No. 198,005 both filed Oct. 17, 1980. The disclosures of these copending applications are hereby incorporated by reference herein.

The description of the embodiments of the present invention contained herein are intended to be taken in an illustratively and not in a limiting sense. Various modifications and changes may be made to the embodiments described herewith without departing from the scope of the present invention as defined by the appended claims.

What is claimed is:

1. A sensing device for use in an apparatus for detecting a substance on the surface of a liquid, said sensing device comprising:
    a mounting surface adapted for facing downwardly toward said liquid surface;
    a plurality of sensing elements each of which is mounted at a different predetermined distance below said mounting surface;
    a mass of floatation material having a circumferential flange forming said mounting surface and a central portion forming a floatation means for supporting said mounting surface at said liquid surface whereby said sensing elements may be maintained at different known depths below said liquid surface.

2. The device of claim 1, further comprising electrical conductors coupled to said sensing elements and wherein said floatation means is adapted for supporting portions of said electrical conductors.

3. The device of claim 1, wherein said circumferential flange includes a substantially larger amount of said floatation material than said central portion.

4. The device of claim 1, wherein the perimeter of said flange is substantially circular.

5. The device of claim 1, wherein said mass of floatation material includes a second surface located on the opposite side of said flange from said mounting surface and facing in the opposite direction from said mounting surface.

6. The device of claim 5, further comprising said electrical conductors coupled to said sensing elements at said second surface.

7. The device of claim 6, further comprising a circumferential ridge located on said second surface for containing a sealing material thereon prior to hardening of said material.

8. The device of claim 7, wherein said sealing material includes an epoxy resin for shielding the coupling between said electrical conductors and said sensing elements to reduce deterioration thereof.

* * * * *